United States Patent
Igarashi et al.

(10) Patent No.: US 6,358,634 B1
(45) Date of Patent: Mar. 19, 2002

(54) NITROGEN-CONTAINING HETEROCYCLIC COMPOUND, ORGANIC LIGHT-EMITTING DEVICE MATERIAL AND ORGANIC LIGHT-EMITTING DEVICE

(75) Inventors: Tatsuya Igarashi; Hisashi Okada, both of Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/504,122

(22) Filed: Feb. 15, 2000

(30) Foreign Application Priority Data

Feb. 15, 1999 (JP) ............................... 11-036107
Nov. 30, 1999 (JP) ............................ 11-340788

(51) Int. Cl.$^7$ ...................... H05B 33/14; C07D 471/02
(52) U.S. Cl. .................. 428/690; 428/704; 428/917; 252/301.16; 252/301.26; 252/301.31; 313/504; 313/506; 546/113; 546/118
(58) Field of Search ................... 428/690, 704, 428/917; 313/504, 506; 252/301.16, 301.26, 301.31; 546/113, 114, 115, 118

(56) References Cited

U.S. PATENT DOCUMENTS

| | | | |
|---|---|---|---|
| 5,755,999 A | 5/1998 | Shi et al. ............... | 252/301.16 |
| 5,779,937 A | * 7/1998 | Sano et al. ............. | 252/301.16 |
| 5,858,560 A | 1/1999 | Nakamura et al. .......... | 428/690 |

* cited by examiner

Primary Examiner—Cynthia H. Kelly
Assistant Examiner—Ling Xu
(74) Attorney, Agent, or Firm—Sughrue Mion, PLLC

(57) ABSTRACT

The present invention provides an organic light-emitting device material such as electron-transporting material and light-emitting material capable of emitting light having a high luminance and color purity. A novel organic light-emitting material is provided comprising a compound having a partial structure represented by the following general formula (I):

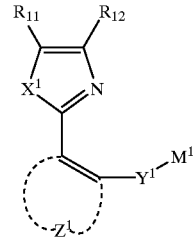

(1)

wherein $R^{11}$ and $R^{12}$ each represent a hydrogen atom or substituent, with the proviso that $R^{11}$ and $R^{12}$ are not bonded to form a benzo condensed ring; $X^1$ represents an oxygen atom, a sulfur atom, a substituted or unsubstituted nitrogen atom or —$C(R^{13})R^{14}$—; $R^{13}$ and $R^{14}$ each represent a hydrogen atom or a substituent; $Y^1$ represents an oxygen atom, a sulfur atom or a substituted or unsubstituted nitrogen atom; $M^1$ represents a metal ion or a hydrogen atom; and $Z^1$ represents an atomic group required to form a 5- or 6-membered ring.

20 Claims, No Drawings

NITROGEN-CONTAINING HETEROCYCLIC COMPOUND, ORGANIC LIGHT-EMITTING DEVICE MATERIAL AND ORGANIC LIGHT-EMITTING DEVICE

FIELD OF THE INVENTION

The present invention relates to a novel nitrogen-containing heterocyclic compound, an organic light-emitting device material comprising such a nitrogen-containing heterocyclic compound and an organic light-emitting device containing such a nitrogen-containing heterocyclic compound.

BACKGROUND OF THE INVENTION

Today, various display devices comprising organic fluorescent materials are under extensive study. Among these display devices, organic EL (electroluminescence) devices can emit light having a high luminance even when driven at a low voltage and thus are noted as favorable display device. For example, an EL device comprising an organic thin film layer formed by evaporation of an organic compound has been known (as disclosed in *Applied Physics Letters*, vol. 51, page 913, 1987). The organic EL device disclosed in the above cited reference has a laminated structure comprising an electron-transporting material and a positive hole-transporting material and thus exhibits drastically improved light-emitting properties as compared with the conventional single-layer devices.

With this report as a turning-point, organic EL devices have been under extensive research and development. Accordingly, the development of electron-transporting materials and hole-transporting materials providing an enhanced light-emitting efficiency have been extensively studied. However, no compounds superior to Alq(Tris(8-hydroxyquinolinato)aluminum) have been found yet in the development of electron-transporting materials. It has thus been desired to provide improved electron-transporting materials. Further, Alq fluoresces green and thus is not appropriate as an electron-transporting material for blue light-emitting device. This, too, is why the development of improved electron-transporting materials has been desired.

Moreover, the application of organic EL devices to full-color display has been recently studied extensively. In order to develop a high performance full-color display, it is necessary to enhance the purity of the colors, i.e., blue, green and red, of light emitted. However, it is difficult to emit light having a high color purity. For example, benzo-condensed nitrogen-containing heterocyclic compounds as disclosed in Seizo Miyata, Organic EL devices and its forefront of industrialization, NTS, page 40, 1998, JP-A-7-133483 (The term "JP-A" as used herein means an "unexamined published Japanese patent application"), and JP-A-10-330744 are widely studied blue light-emitting materials but can emit only a blue light having a low color purity. It has thus been desired to provide organic EL devices having an improved color purity.

SUMMARY OF THE INVENTION

It is therefore an object of the present invention to provide an organic light-emitting device material such as electron-transporting material and light-emitting material capable of emitting light having a high luminance and a high color purity.

The foregoing object of the present invention will become apparent from the following detailed description and examples.

The foregoing object of the present invention is accomplished by the following aspects of the present invention:

(1) An organic light-emitting device material comprising a compound having a partial structure represented by the following general formula (I):

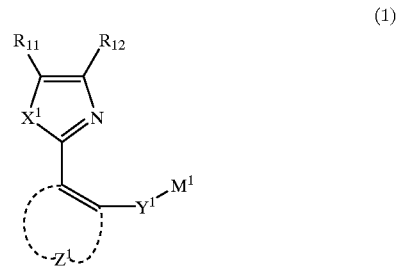

(I)

wherein $R^{11}$ and $R^{12}$ each represent a hydrogen atom or a substituent, with the proviso that $R^{11}$ and $R^{12}$ are not bonded to form a benzo condensed ring; $X^1$ represents an oxygen atom, a sulfur atom, a substituted or unsubstituted nitrogen atom or —$C(R^{13})R^{14}$—; $R^{13}$ and $R^{14}$ each represent a hydrogen atom or a substituent; $Y^1$ represents an oxygen atom, a sulfur atom or a substituted or unsubstituted nitrogen atom; $M^1$ represents a metal ion or a hydrogen atom; and $Z^1$ represents an atomic group required to form a 5- or 6-membered ring.

(2) An organic light-emitting device material comprising a compound having a partial structure represented by the following general formula (II):

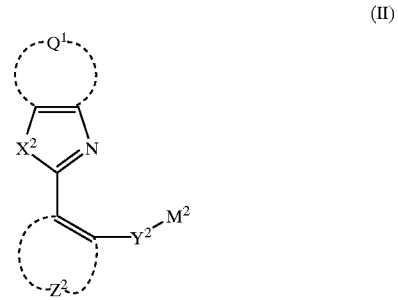

(II)

wherein $Q^1$ represents an atomic group required to form a heterocyclic group; $X^2$ represents an oxygen atom, a sulfur atom, a substituted or unsubstituted nitrogen atom or —$C(R^{15})R^{16}$—; $R^{15}$ and $R^{16}$ each represent a hydrogen atom or a substituent; $Y^2$ represents an oxygen atom, a sulfur atom or a substituted or unsubstituted nitrogen atom; $M^2$ represents a metal ion or a hydrogen atom; and $Z^2$ represents an atomic group required to form a 5- or 6-membered ring.

(3) A compound represented by the following general formula (III):

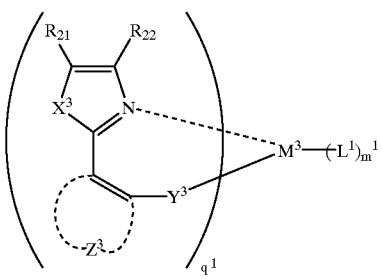

(III)

wherein $R^{21}$ and $R^{22}$ each represent a hydrogen atom, an alkyl group, an aryl group or a heteroaryl group; $X^3$ represents an oxygen atom, a sulfur atom, a substituted or unsubstituted nitrogen atom or —$C(R^{23})R^{24}$—; $R^{23}$ and $R^{24}$ each represent a hydrogen atom or a substituent; $Y^3$ represents an oxygen atom, a sulfur atom or a substituted or unsubstituted nitrogen atom; $M^3$ represents a metal ion; $q^1$ represents an integer of not less than 1; $L^1$ represents a ligand; me represents an integer of not less than 0; and $Z^3$ represents an atomic group required to form a 5- or 6-membered ring.

(4) A compound represented by the following general formula (IV):

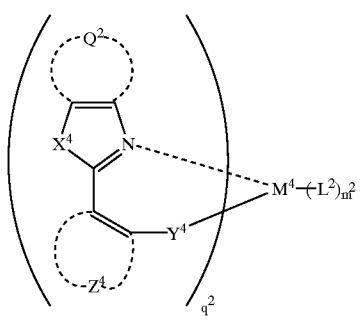

(IV)

wherein $Q^2$ represents an atomic group required to form a heterocyclic group; $X^3$ represents an oxygen atom, a sulfur atom, a substituted or unsubstituted nitrogen atom or —$C(R^{25})R^{26}$—; $R^{25}$ and $R^{26}$ each represent a hydrogen atom or a substituent; $Y^4$ represents an oxygen atom, a sulfur atom or a substituted or unsubstituted nitrogen atom; $M^4$ represents a metal ion; $q^2$ represents an integer of not less than 1; $L^2$ represents a ligand; $m^2$ represents an integer of not less than 0; and $Z^4$ represents an atomic group required to form a 5- or 6-membered ring.

(5) An organic light-emitting device comprising a pair of electrodes having a light-emitting layer or a plurality of organic thin film layers containing said light-emitting layer formed interposed therebetween, wherein at least one of said plurality of organic thin film layers comprises at least one of compounds defined in the foregoing aspects (1) to (4) of the present invention incorporated therein.

(6) The organic light-emitting device according to the aspect (5), wherein at least one of said plurality of organic thin film layers is formed by a coating process.

DETAILED DESCRIPTION OF THE INVENTION

The foregoing compound of the present invention is a compound having a partial structure represented by the general formula (I). The compound having a partial structure represented by the general formula (I) is preferably a metallic complex. Such a metallic complex may be a compound having at least one partial structure represented by the general formula (I) incorporated therein. The metallic complex may also be a so-called polynuclear complex having a plurality of metal specifies per molecule. Further, the metallic complex may have a plurality of ligands. More preferably, the compound of the present invention is a neutral metallic complex.

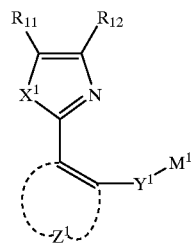

(1)

The general formula (I) will be further described hereinafter.

$R^{11}$ and $R^{12}$ each represent a hydrogen atom or a substituent. Examples of the substituent represented by $R^{11}$ or $R^{12}$ include an alkyl group (preferably $C_{1-20}$ (wherein "$C_{1-20}$", means 1 to 20 carbon atoms, hereinafter the same), more preferably $C_{1-12}$, particularly $C_{1-8}$ alkyl group such as methyl, ethyl, iso-propyl, tert-butyl, n-octyl, n-decyl, n-hexadecyl, cyclopropyl, cyclopentyl and cyclohexyl), an alkenyl group (preferably $C_{2-20}$, more preferably $C_{2-12}$, particularly $C_{2-8}$ alkenyl group such as vinyl, allyl, 2-butenyl and 3-pentenyl), an alkinyl group (preferably $C_{2-20}$, more preferably $C_{2-12}$, particularly $C_{2-8}$ alkinyl group such as propargyl and 3-pentinyl), an aryl group (preferably $C_{6-30}$, more preferably $C_{6-20}$, particularly $C_{6-12}$ aryl group such as phenyl, p-methylphenyl and naphthyl), a substituted carbonyl group (preferably $C_{1-20}$, more preferably $C_{1-16}$, particularly $C_{1-12}$ substituted carbonyl group such as acetyl, benzoyl, methoxycarbonyl, phenyloxycarbonyl, dimethylaminocarbonyl and phenylaminocarbonyl), an amino group (preferably $C_{0-20}$, more preferably $C_{1-16}$, particularly $C_{1-12}$ amino group such as dimethylamino, methylcarbonylamino, ethylsulfonylamino, dimethylaminocarbonylamino and phthalimide), a sulfonyl group (preferably $C_{1-20}$, more preferably $C_{1-16}$, particularly $C_{1-12}$ sulfonyl group such as mesyl and tosyl), a sulfo group, a carboxyl group, a heterocyclic group (e.g., aliphatic heterocyclic group, aromatic heterocyclic group, preferably $C_{1-50}$ so more preferably $C_{1-30}$, particularly $C_{2-12}$ heterocyclic group preferably containing any of oxygen atom, sulfur atom and nitrogen atom such as imidazolyl, pyridyl, furyl, piperidyl, morpholino, benzoxazolyl and triazolyl), a hydroxyl group, an alkoxyl group (preferably $C_{1-20}$, more preferably $C_{1-16}$, particularly $C_{1-12}$ alkoxyl group such as methoxy and benzyloxy), an aryloxy group (preferably $C_{6-20}$, more preferably $C_{6-16}$ particularly $C_{6-12}$ aryloxy group such as phenoxy and naphthyloxy), a halogen atom (preferably fluorine, chlorine, bromine, iodine), a thiol group, an alkylthio group (preferably $C_{1-20}$, more preferably $C_{1-16}$, particularly $C_{1-12}$ alkylthio group such as methylthio), an arylthio group (preferably $C_{6-20}$, more preferably $C_{6-16}$, particularly $C_{6-12}$ arylthio group such as phenylthio), a cyano group, and a silyl group (preferably $C_{0-40}$, more preferably $C_{3-30}$, particularly $C_{3-18}$ silyl group such as trimethylsilyl, triphenylsilyl and t-butyldiphenylsilyl). These substituents may be further substituted.

$R^{11}$ and $R^{12}$ may be connected to each other to form a ring (such as a heterocyclic group (preferably $C_{2-20}$, more preferably $C_{3-12}$, particularly $C_{3-8}$ heterocyclic group containing as hetero atom nitrogen atom, oxygen atom, sulfur atom or selenium atom, such as heterocyclic group represented by $Q^1$ shown later) and particularly $C_{2-8}$ alkinyl group such as propargyl and 3-pentinyl), an aryl group (preferably $C_{6-30}$, more preferably $C_{6-20}$, particularly $C_{6-12}$ aryl group such as phenyl, p-methylphenyl and naphthyl), a substituted carbonyl group (preferably $C_{1-40}$, more preferably $C_{1-20}$, particularly $C_{1-12}$ substituted carbonyl group such as acetyl, benzoyl, methoxycarbonyl, dimethylaminocarbonyl and phenylamino carbonyl), a substituted sulfonyl group (preferably $C_{1-20}$, more preferably $C_{1-16}$, particularly $C_{1-12}$ substituted sulfonyl group such as mesyl and tosyl), and a heterocyclic group (preferably $C_{1-20}$, more preferably $C_{1-16}$ particularly $C_{1-12}$ heterocyclic group preferably having any of oxygen atom, sulfur atom and nitrogen atom, such as imidazolyl, pyridyl, furyl and piperidyl). These substituents may be further substituted. Preferred among these substituents on nitrogen are an alkyl group, an aryl group and an aromatic heterocyclic group. Particularly preferred among these substituents are an alkyl group and an aryl group.

$R^{13}$ and $R^{14}$ each preferably are a hydrogen atom, an alkyl group or an aryl group, more preferably a hydrogen atom or an alkyl group, particularly an alkyl group.

$X^1$ is preferably an oxygen atom, a sulfur atom or a substituted or unsubstituted nitrogen atom, more preferably an oxygen atom or a substituted nitrogen atom, even more preferably an oxygen atom, an alkyl group-substituted nitrogen atom or an aryl group-substituted nitrogen atom, particularly preferably an aryl group-substituted nitrogen atom.

$Y^1$ represents an oxygen atom, a sulfur atom or a a cycloalkene ring (preferably $C_{4-20}$, more preferably $C_{5-12}$, particularly $C_{5-8}$ cycloalkene ring such as cyclohexene ring and cyclopentene ring)). However, $R^{11}$ and $R^{12}$ are not connected to each other to form a benzo condensed ring (including benzene ring, naphthalene ring and anthracene ring).

$R^{11}$ and $R^{12}$ each preferably are a hydrogen atom, an alkyl group, an aryl group, an aromatic heterocyclic group or one of groups which are connected to each other to form a heterocyclic group, more preferably a hydrogen atom, an alkyl group, an aryl group or one of groups which are connected to each other to form a heterocyclic group, particularly a hydrogen atom, an aryl group or one of groups which are connected to each other to form a heterocyclic group.

$X^1$ represents an oxygen atom, a sulfur atom, a substituted or unsubstituted nitrogen atom or —$CR^{13}(R^{14})$—.

The term "unsubstituted nitrogen atom" as used herein is meant to indicate —NH—.

$R^{13}$ and $R^{14}$ each represent a hydrogen atom or a substituent. Examples of such a substituent include those described with reference to $R^{11}$. Examples of the substituent on nitrogen include an alkyl group (preferably $C_{1-20}$, more preferably $C_{1-12}$, particularly $C_{1-8}$ alkyl group such as methyl, ethyl, iso-propyl, tert-butyl, n-octyl, n-decyl, n-hexadecyl, cyclopropyl, cyclopentyl and cyclohexyl), an alkenyl group (preferably $C_{2-20}$, more preferably $C_{2-12}$, particularly $C_{2-8}$ alkenyl group such as vinyl, allyl, 2-butenyl and 3-pentenyl), an alkinyl group (preferably $C_{2-20}$, more preferably $C_{2-12}$, substituted or unsubstituted nitrogen atom. Examples of the substituent on nitrogen include those described with reference to $X^1$. Preferred among these substituents are a substituted sulfonyl group and a substituted carbonyl group. More desirable among these substituents is a substituted sulfonyl group. Even more desirable among these substituents is an arylsulfonyl group.

Preferred among the groups represented by $Y^1$ are an oxygen atom and a substituted nitrogen atom. Even more desirable among these groups is an oxygen atom.

$Z^1$ represents an atomic group required to form a 5- or 6-membered ring. The ring containing $Z^1$ may have substituents (Examples of these substituents include those described with reference to substituent on $R^{11}$) or may be condensed to other rings.

Examples of the ring containing $Z^1$ include cyclopentene, cyclohexene, benzene, naphthalene, anthracene, phenanthrene, pyrene, perylene, pyridine, quinoline, furan, thiophene, pyrazine, pyrimidine, thiazole, benzothiazole, naphthothiazole, oxazole, benzoxaole, naphthoxazole, isoxazole, selenazole, benzoselenazole, naphthoselenazole, imidazole, benzoimidazole, naphthoimidazole, isoquinoline, pyrazole, and triazole.

The ring containing $Z^1$ is preferably an aromatic ring. Preferred examples of such an aromatic ring include benzene, naphthalene, anthracene, pyridine, thiophene, pyrazine, and pyrimidine. More desirable among these aromatic rings are benzene and naphthalene. Even more desirable among these aromatic rings is benzene.

$M^1$ represents a metal ion or a hydrogen atom. $M^1$ is preferably a metal ion. The metal ion represented by $M^1$ is not specifically limited but is preferably a divalent or trivalent metal ion, more preferably $Be^{2+}$, $Mg^{2+}$, $Al^{3+}$ or $Zn^{2+}$, even more preferably $Al^{3+}$ or $Zn^{2+}$.

A preferred embodiment of the partial structure represented by the general formula (I) is the following general formula (II):

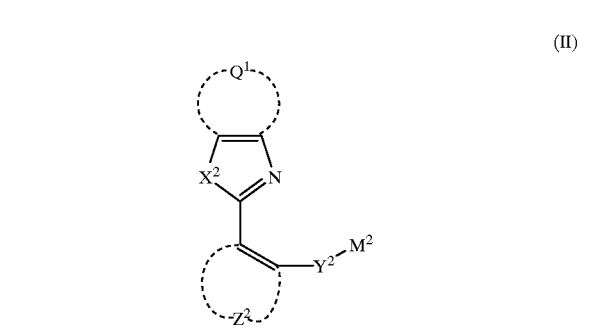

(II)

The general formula (II) will be further described hereinafter. $Q^1$ represents a group required to form a heterocyclic group (e.g., aliphatic heterocyclic group, aromatic heterocyclic group, preferably $C_{2-20}$, more preferably $C_{3-15}$, particularly $C_{4-10}$ heterocyclic group preferably containing any of oxygen atom, sulfur atom and nitrogen atom, such as pyridine ring, pyrazine ring, pyrimidine ring, quinoline ring, indole ring, furan ring, pyran ring, pyrrole ring, imidazole ring, pyrazole ring, thiophene ring, dihydropyran ring and dihydropyridine). $Q^1$ may have a substituent thereon. Examples of the substituent on $Q^1$ include those described with reference to $R^{11}$. Preferred among the heterocyclic groups formed by $Q^1$ are pyridine ring, pyrazine ring, and pyrimidine ring. More desirable among these heterocyclic groups are pyridine ring and pyrazine ring. Even more desirable among these heterocyclic groups is pyridine ring.

$X^2$, $Z^2$, $Y^2$ and $M^2$ in the general formula (II) have the same meaning and preferred range as $X^1$, $Z^1$, $Y^1$ and $M^1$ in the general formula (I).

The number of metal ions in the metallic complex having a partial structure represented by the general formula may be one or plural. The number of the kinds of metal ions may be one or plural. The metallic complex is preferably one containing two or less metal ions of two or less kinds, more preferably two or less metal ion of one kind, even more preferably one metal ion of one kind.

The number of the kinds of ligands in the metallic complex having a partial structure represented by the general formula (I) may be one or plural. The number of the kinds of ligands in the metallic complex is preferably from 1 to 3, more preferably 1 or 2, and further more preferably 1 (only one ligand derived from the partial structure represented by the general formula (I)). An example of ligands other than the ligand derived from the partial structure represented by the general formula (I) is $L^1$ shown below.

The metallic complex having a partial structure represented by the general formula (I) preferably fluoresces at a maximum wavelength ($\lambda$max) of from not less than 370 nm to not more than 490 nm, more preferably from not less than 390 nm to not more than 470 nm, even more preferably from not less than 390 nm to not more than 450 nm.

The compound of the present invention (preferably compound having a partial structure represented by the general formula (I), preferably compound having a partial structure represented by the general formula (II)) is preferably a metallic complex represented by the general formula (III) (more preferably a metallic complex represented by the general formula (IV)), more preferably a metallic complex represented by the general formula (V)(preferably a metallic complex represented by the general formula (VI)), even more preferably a metallic complex represented by the general formula (VII) (preferably a metallic complex represented by the general formula (VIII)), particularly a metallic complex represented by the general formula (IX) or (X).

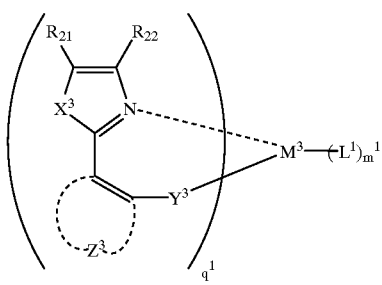

(III)

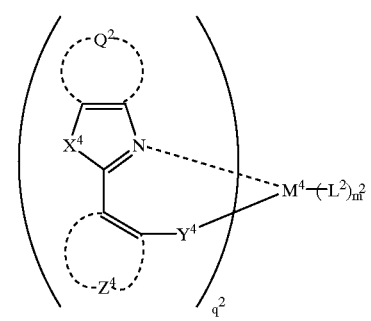

(IV)

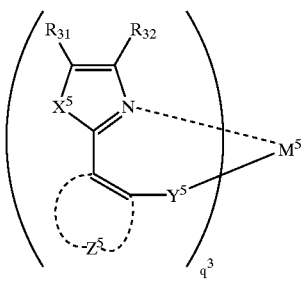

(V)

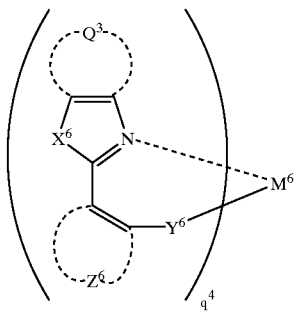

(VI)

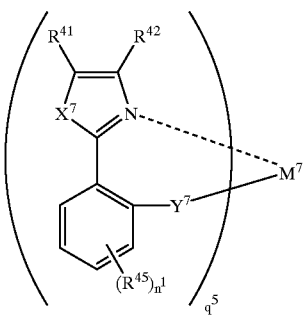

(VII)

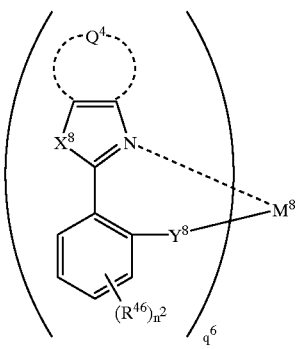

(VIII)

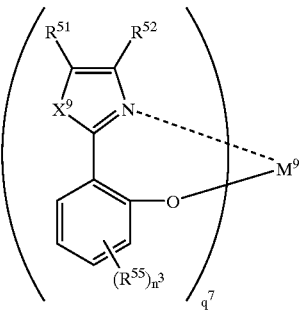

(IX)

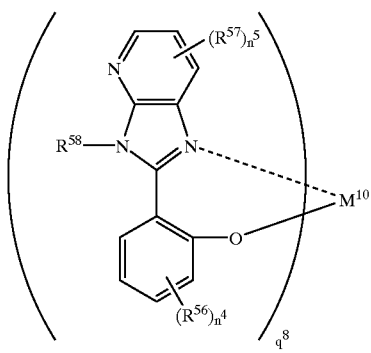

(X)

The general formula (III) will be further described hereinafter.

$Z^3$, $X^3$ and $Y^3$ have the same meaning and preferred range as $Z^1$, $X^1$ and $Y^1$, respectively. $R^{21}$ and $R^{22}$ each represent a hydrogen atom, an alkyl group, an aryl group or a heteroaryl group, preferably an alkyl group or an aryl group, more preferably an aryl group. $M^3$ represents a metal ion. The metal ion represented by $M^3$ has the same examples and preferred range as the metal ion represented by $M^1$.

$L^1$ represents a unidentate or multidentate ligand. Examples of such a ligand include a halogen ion (e.g., Cl⁻, Br⁻, I⁻), a perchlorate ion, an alkoxy ion (preferably $C_{1-20}$, more preferably $C_{1-10}$, even more preferably $C_{1-5}$ alkoxy ion such as methoxy ion, ethoxy ion, isopropoxy ion and acetylacetone ion), an aryloxy ion (preferably $C_{6-20}$, more preferably $C_{6-12}$, even more preferably $C_{6-8}$ aryloxy ion such as phenoxy ion, quinolinol ion and 2-(2-hydroxyphenyl)benazole ion), a nitrogen-containing heterocyclic group (preferably, $C_{1-20}$, more preferably $C_{2-10}$, even more preferably $C_{3-8}$ nitrogen-containing heterocyclic group such as phenanthrene and bipyridyl), an acyloxy ion (preferably $C_{1-20}$ more preferably $C_{2-10}$, even more preferably $C_{3-8}$ acyloxy group such as acetyloxy ion), an ether compound (preferably $C_{2-20}$, particularly $C_{3-10}$, even more preferably $C_{3-8}$ ether compound such as tetrahydrofuran), and a hydroxy ion. Preferred among these ligands are an alkoxy ion, and an aryloxy ion. Particularly preferred among these ligands is an aryloxy ion.

The suffix $q^1$ represents an integer of not less than 1, and the suffix $m^1$ represents an integer of not less than 0. The preferred range of $q^1$ and $m^1$ depend on the kind of metal ion and is not specifically limited. In practice, however, $q^1$ is preferably from 1 to 4, more preferably from 1 to 3, particularly from 2 or 3, and $m^1$ is preferably from 0 to 2, more preferably 0 or 1, particularly 0. The combination of $q^1$ and $m^1$ is preferably such that the metallic complex represented by the general formula (III) is a neutral complex.

The general formula (IV) will be further described hereinafter.

$X^4$, $Y^4$, $Z^4$, $Q^2$, $M^4$, $L^2$, $q^2$ and $m^2$ have the same meaning and preferred range as $X^2$, $Y^2$, $Z^2$, $Q^1$, $M^3$, $L^1$, $q^1$ and $m^1$, respectively.

The general formula (V) will be further described hereinafter.

$R^{31}$, $R^{32}$, $Z^5$, $X^5$, $Y^5$ and $M^5$ have the same meaning and preferred range as $R^{21}$, $R^{22}$, $Z^1$, $X^1$, $Y^1$ and $M^3$, respectively. The suffix $q^3$ represents an integer of not less than 2, preferably 2, 3 or 4, more preferably 2 or 3.

The general formula (VI) will be further described hereinafter.

$X^6$, $Y^6$, $Z^6$, $Q^3$, $M^6$ and $q^4$ have the same meaning and preferred range as $X^2$, $Y^2$, $Z^2$, $Q^1$, $M^4$ and $q^3$, respectively.

The general formula (VII) will be further described hereinafter.

$R^{41}$, $R^{42}$, $X^7$, $Y^7$, $M^7$ and $q^5$ have the same meaning and preferred range as $R^{21}$, $R^{22}$, $X^1$, $Y^1$, $M^3$ and $q^3$ respectively. $R^{45}$ represents a substituent. Examples of the substituent include those described with reference to substituent on $R^{11}$. $R^{45}$ is preferably an alkyl group, an alkenyl group, an aryl group, a heteroaryl group, an alkoxy group or a cyano group, more preferably an alkyl group or an aryl group, even more preferably an alkyl group. The suffix $n^1$ represents an integer of from 0 to 4, preferably 0 or 1, more preferably 0.

The general formula (VIII) will be further described hereinafter.

$X^8$, $Y^8$, $Q^4$, $M^8$, $q^6$, $R^{46}$ and $n^2$ have the same meaning and preferred range as $X^2$, $Y^2$, $Q^1$, $M^3$, $q^3$, $R^{45}$ and $n^1$, respectively.

The general formula (IX) will be further described hereinafter. $R^{51}$, $R^{52}$, $X^9$, $M^9$, $q^7$, $R^{55}$ and $n^3$ have the same meaning as $R^{21}$, $R^{22}$, $X^1$, $M^7$, $q^5$, $R^{45}$ and $n^1$.

The general formula (X) will be further described hereinafter.

$M^{10}$, $q^8$, $R^{56}$ and $n^4$ have the same meaning and preferred range as $M^3$, $q^3$, $R^{45}$ and $n^1$, respectively. $R^{57}$ represents a substituent. The substituent represented by $R^{57}$ has the same examples and preferred range as $R^{56}$. The suffix $n^5$ represents an integer of from 0 to 3, preferably 0 or 1, more preferably 0. $R^{58}$ represents a substituent. Examples of the substituent represented by $R^{58}$ include those described with the substituent on nitrogen of $X^1$. $R^{58}$ is preferably an alkyl group, an aryl group or a heteroaryl group, more preferably an aryl group.

The compound of the present invention may be a polymer compound but is preferably a low molecular weight compound.

Examples of the compound of the present invention will be given below, but the present invention should not be construed as being limited thereto.

(1-1)

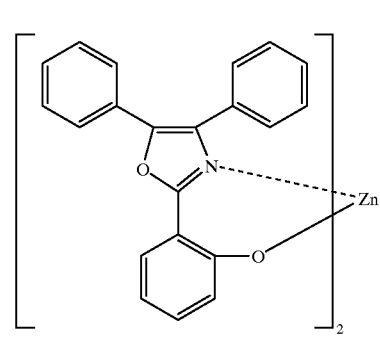

-continued
(1-2)
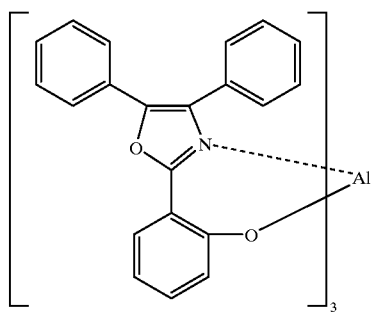
(1-3)
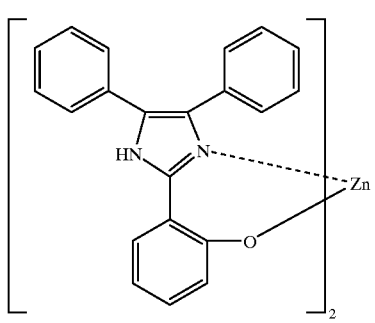
(1-4)
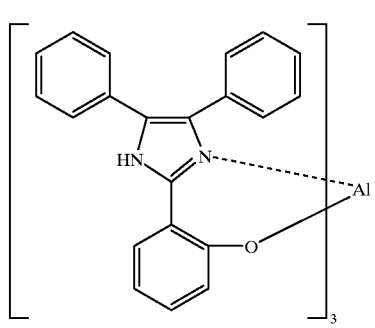
(1-5)
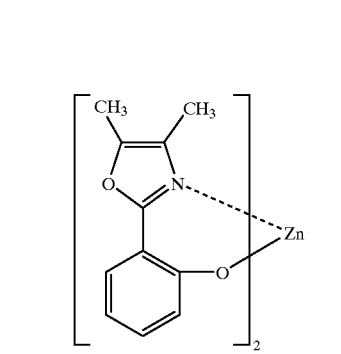
(1-6)
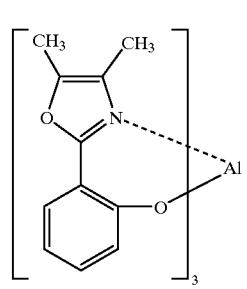
-continued
(1-7)
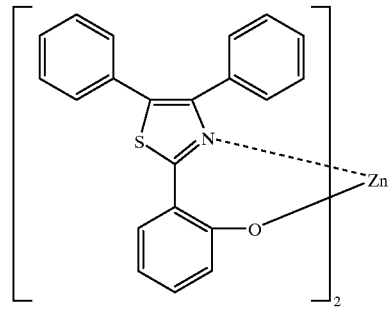
(1-8)
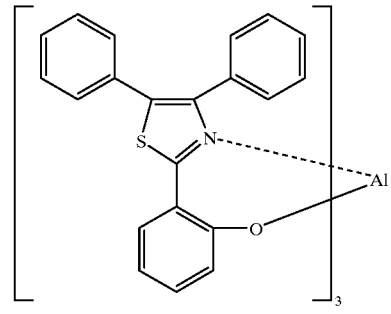
(1-9)
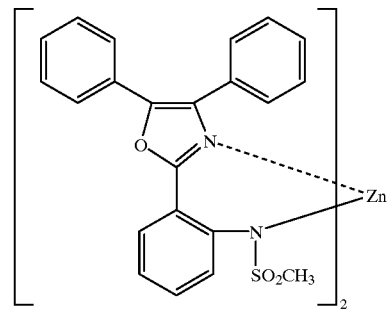
(1-10)
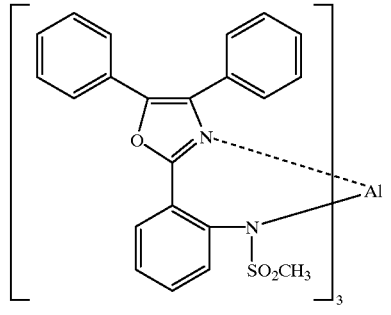
(1-11)
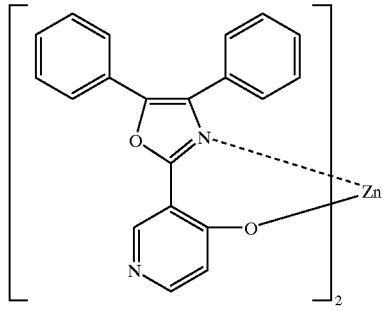

(1-12)
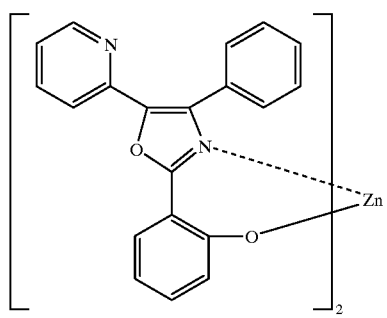
(1-13)
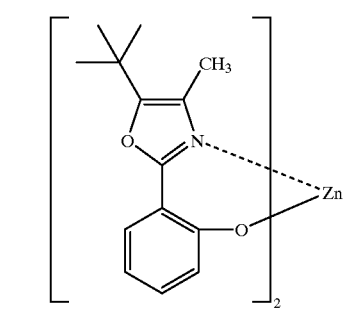
(1-14)
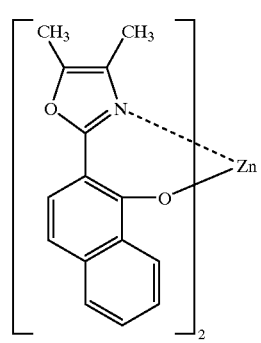
(1-15)
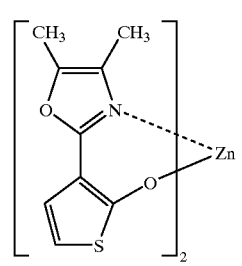
(1-16)
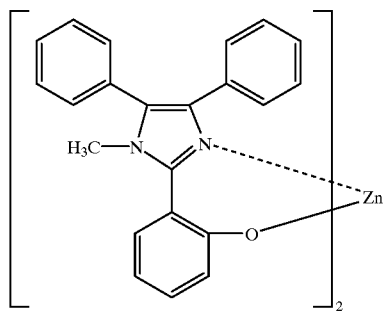
(1-17)
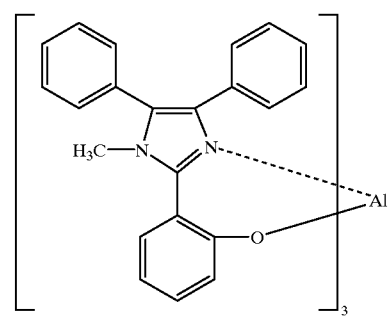
(1-18)
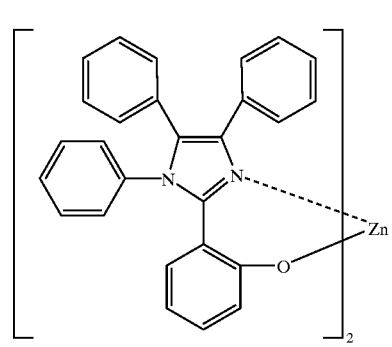
(1-19)
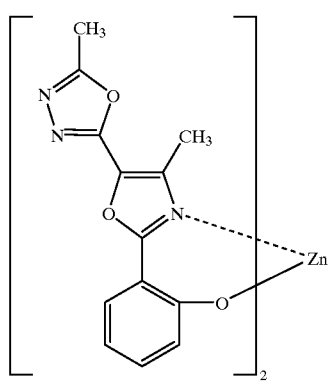
(1-20)
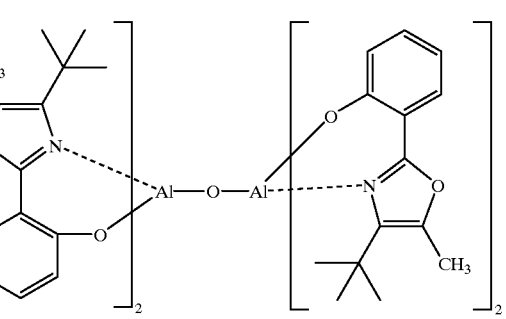

(1-21)
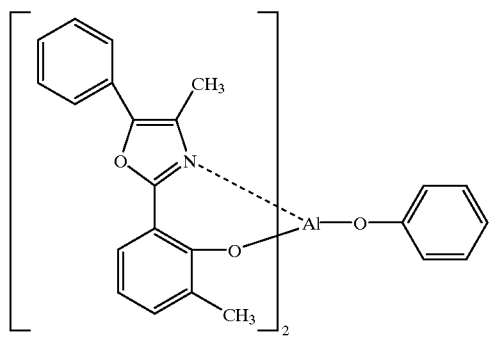
(1-22)
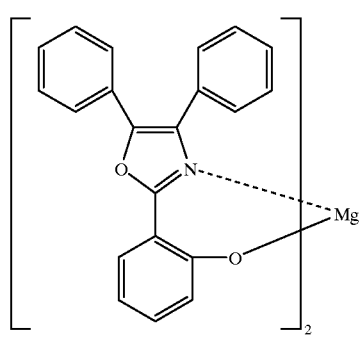
(1-23)
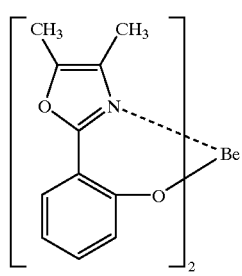
(1-24)
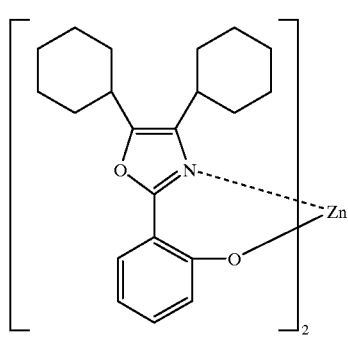
(1-25)
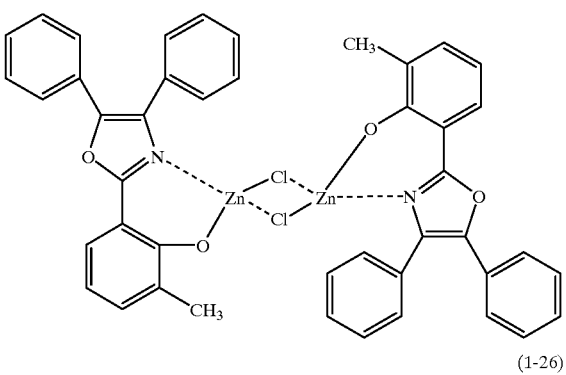
(1-26)
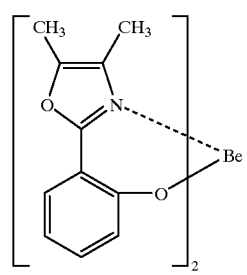
(1-27)
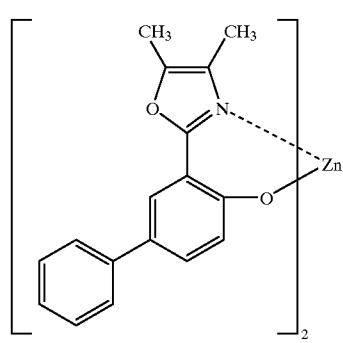
(1-28)
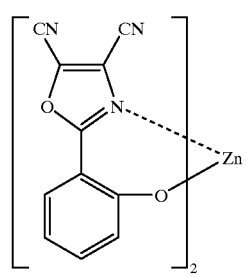
(1-29)
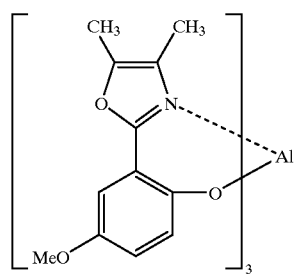

-continued
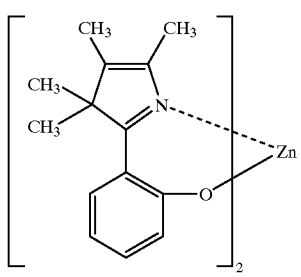
(1-30)
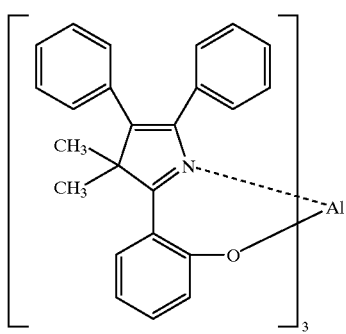
(1-31)
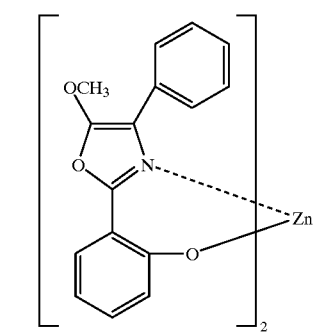
(1-32)
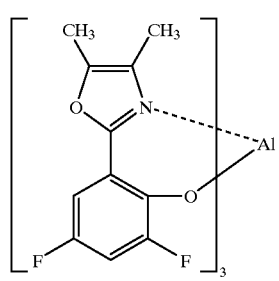
(1-33)
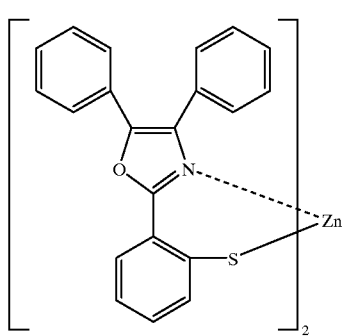
(1-34)
-continued
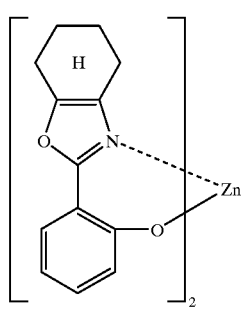
(1-35)
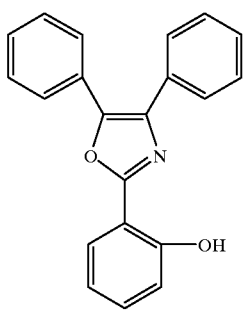
(1-36)
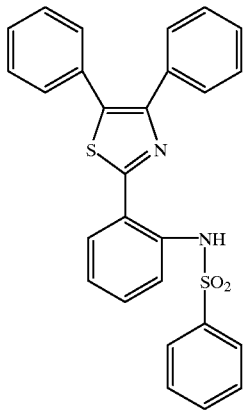
(1-37)
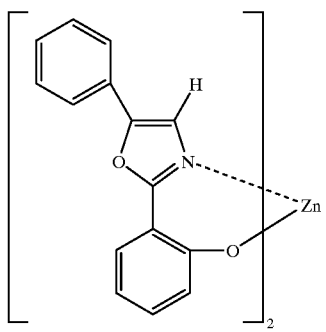
(1-38)

-continued
(2-1)
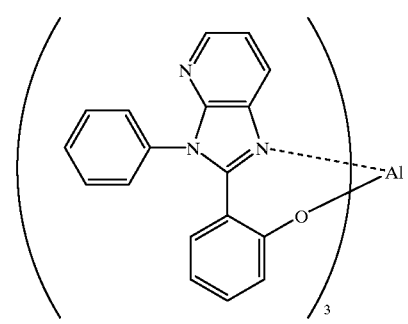
(2-2)
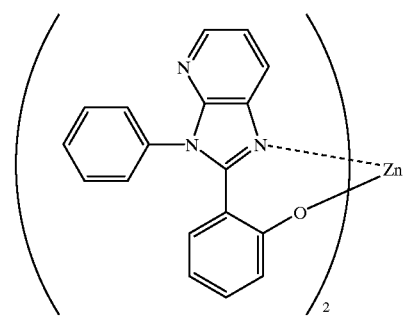
(2-3)
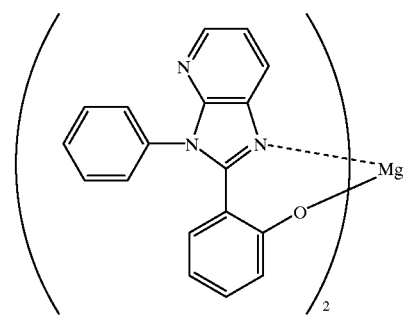
(2-4)
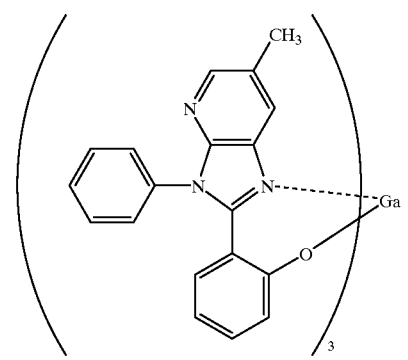
(2-5)
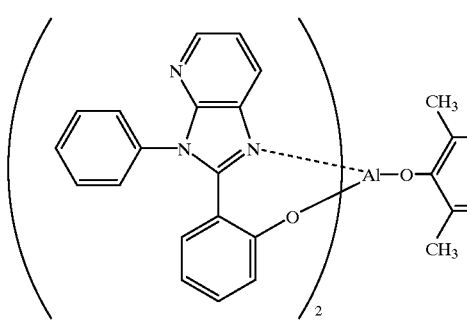
-continued
(2-6)
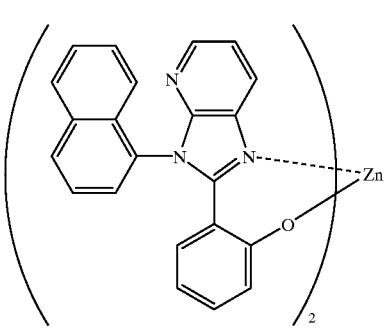
(2-7)
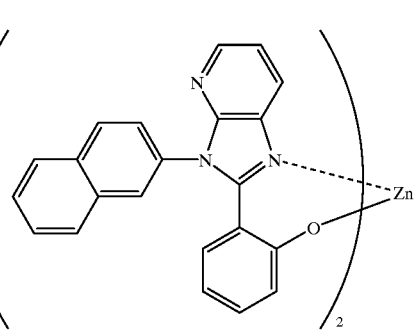
(2-8)
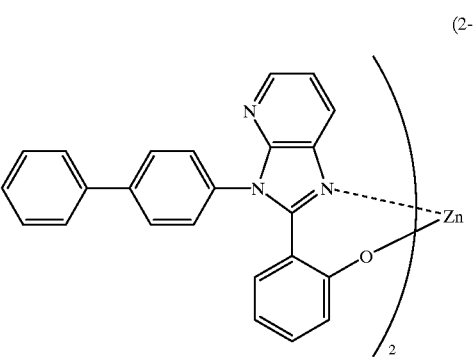
(2-9)
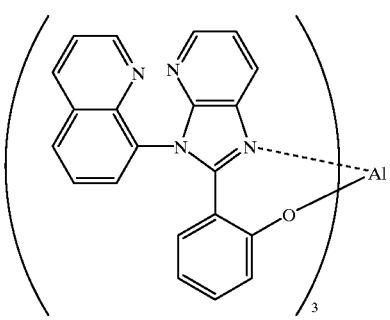
(2-10)
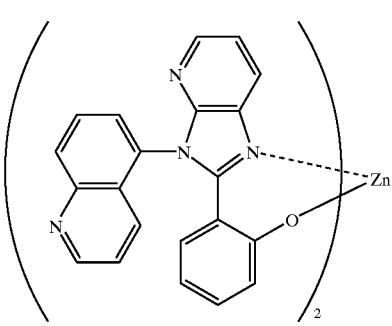

(2-11)
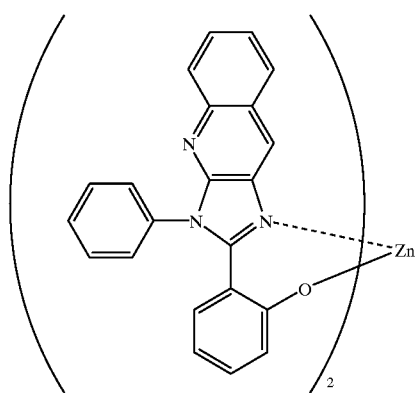
(2-12)
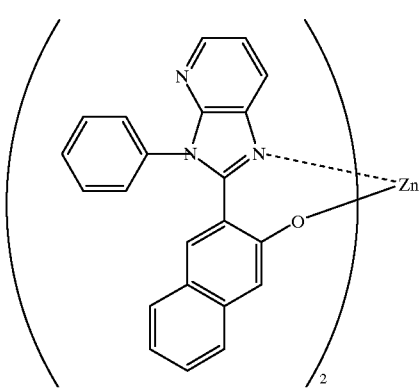
(2-13)
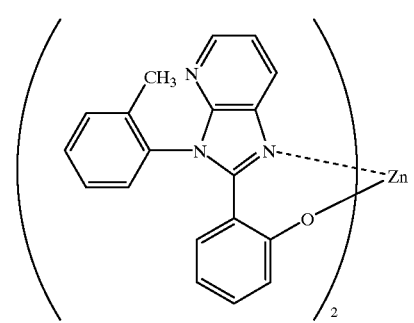
(2-14)
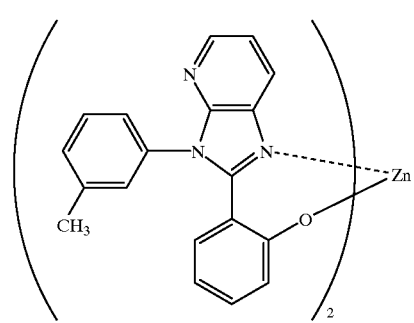
(2-15)
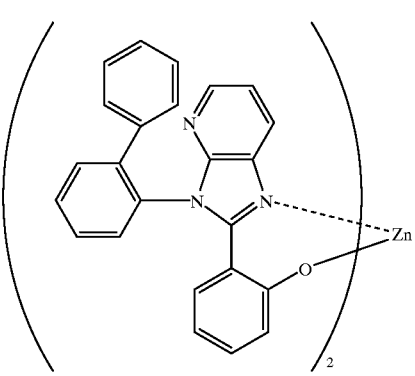
(2-16)
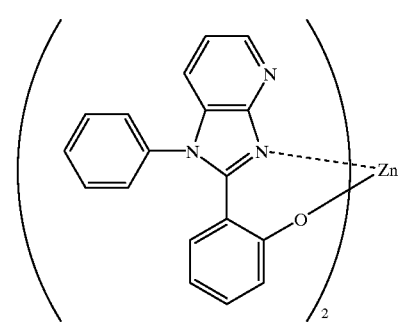
(2-17)
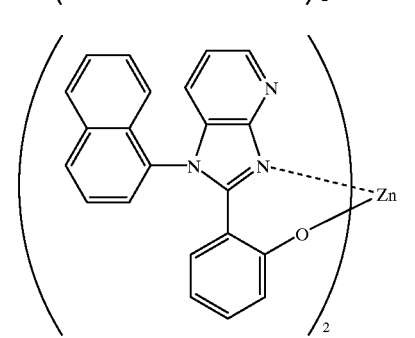
(2-18)
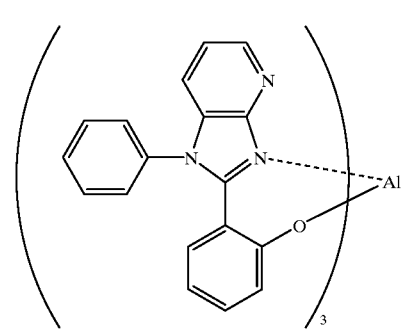
(2-19)

(2-20) 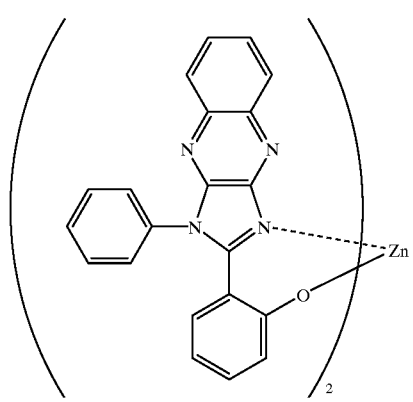
(2-21) 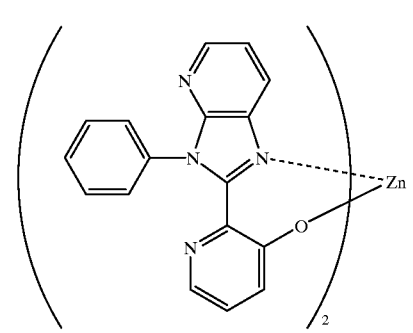
(2-22) 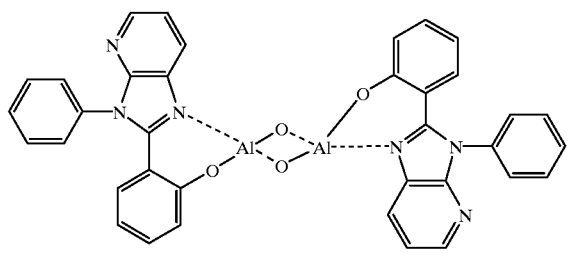
(2-23) 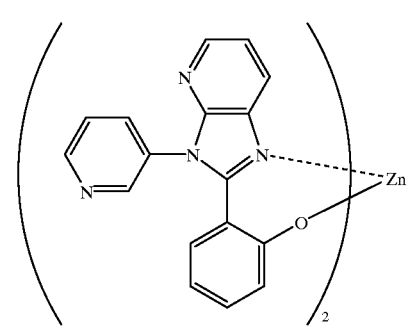
(2-24) 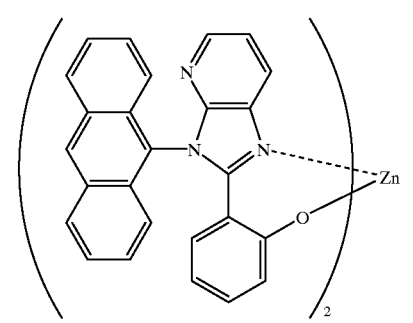
(2-25) 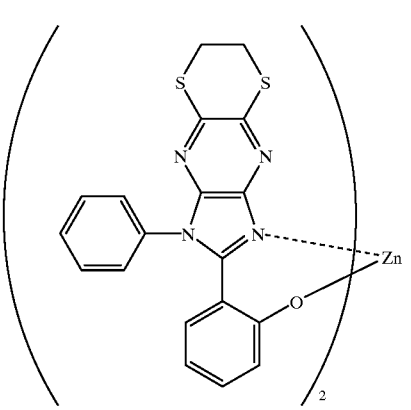
(2-26) 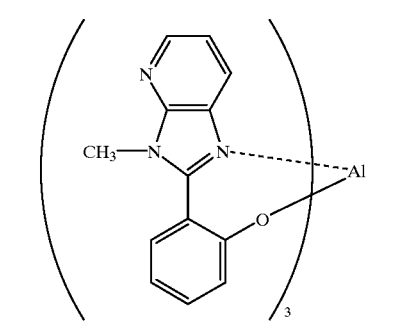
(2-27) 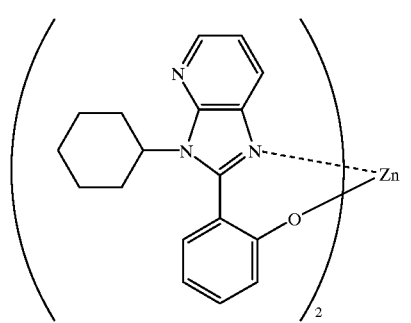
(2-28) 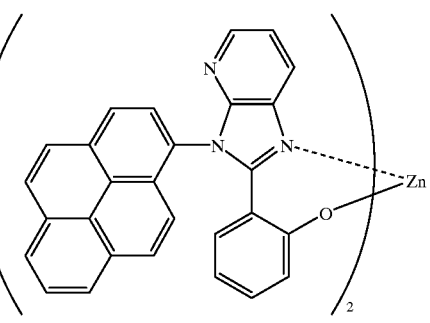

-continued
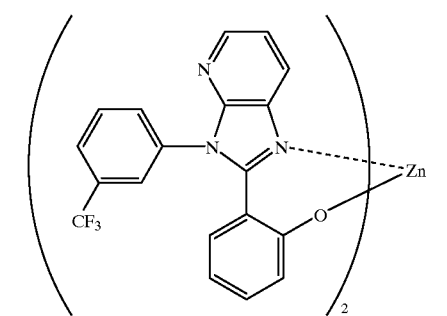
(2-29)
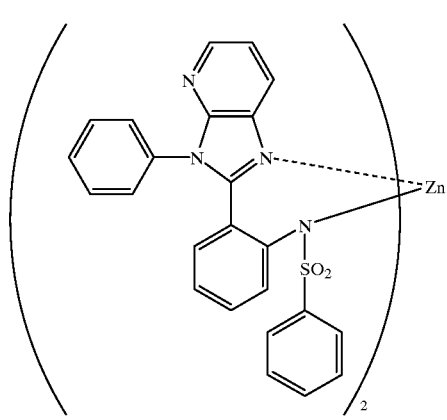
(2-30)
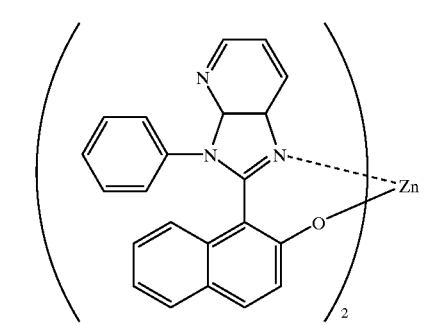
(2-31)
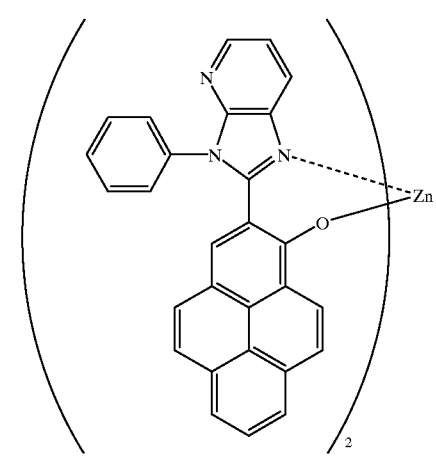
(2-32)
-continued
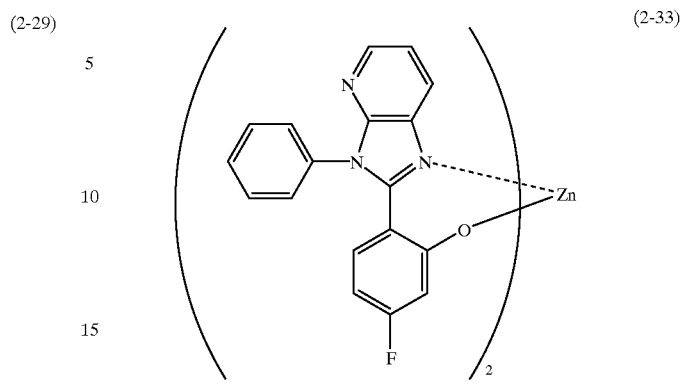
(2-33)
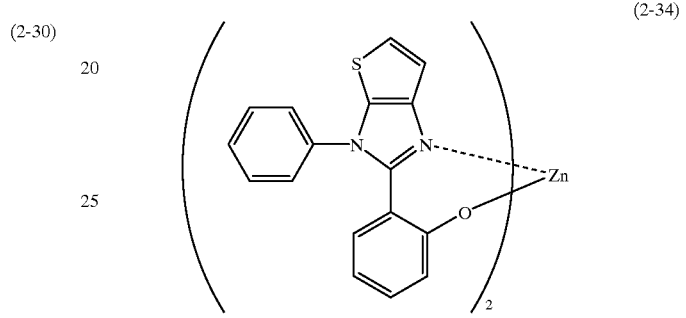
(2-34)
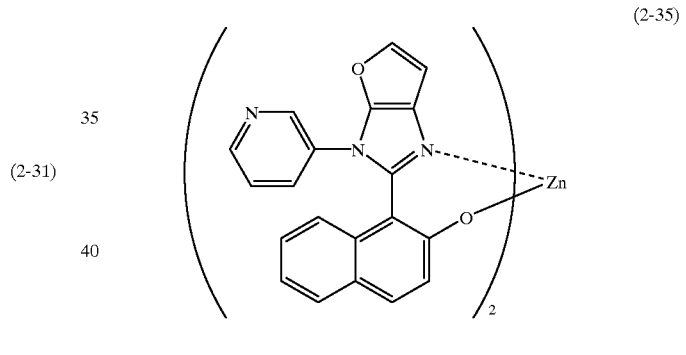
(2-35)
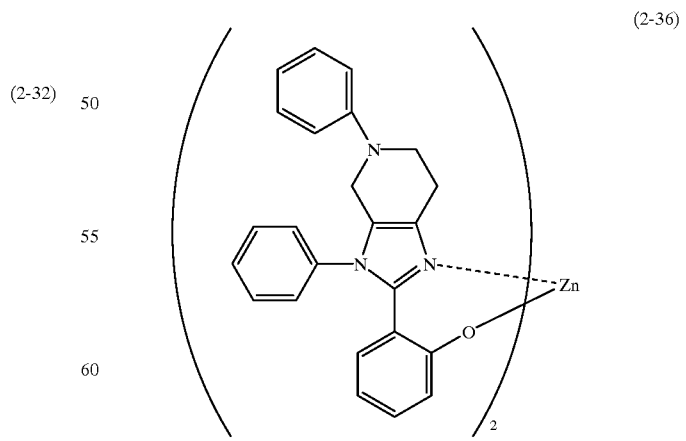
(2-36)
The compound of the present invention can be prepared in accordance with a known synthesis method as disclosed in JP-A-10-330744.

The organic light-emitting device comprising a compound of the present invention will be further described hereinafter. The organic light-emitting device of the present invention is not limited in system, driving method, application, etc. so far as it utilizes the emission of light from the compound of the present invention. A representative example of the organic light-emitting device of the present invention is an organic EL (electroluminescence) device.

The present invention will be further described with reference to the organic EL device comprising a compound of the present invention.

As described in *Applied Physics Letters*, vol. 51, page 913, 1987, the organic EL device preferably comprises an organic layer having a laminated structure. The method for the preparation of the organic layer in the EL device comprising a compound of the present invention is not specifically limited. In practice, however, resistance heating metallizing method, electron beam method, sputtering method, molecular lamination method, coating method, ink jet method, etc. can be used. From the standpoint of properties and preparation, resistance heating metallizing method or coating method is preferred.

The light-emitting device of the present invention is a device comprising a pair of electrodes, i.e., anode and cathode, having a light-emitting layer or a plurality of organic thin film layers containing said light-emitting layer formed interposed therebetween. Besides the light-emitting layer, a positive hole-injecting layer, a positive hole-transporting layer, an electron-injecting layer, an electron-transporting layer, a protective layer, etc. may be incorporated in the light-emitting device of the present invention. These layers each may have additional functions. These layers each may be formed by various materials.

The anode supplies positive holes into the positive hole-injecting layer, positive hole-transporting layer, light-emitting layer, etc. The anode can be made of a metal, alloy, metal oxide, electrically-conductive compound or mixture thereof preferably, a material having a work function of not less than 4e is used. Specific examples of such a material include electrically-conductive metal oxide such as tin oxide, zinc oxide, indium oxide and indium tin oxide (ITO), metal such as gold, silver, chromium and nickel, mixture or laminate of such a metal and electrically-conductive metal oxide, inorganic electrically-conductive material such as copper iodide and copper sulfide, organic electrically-conductive material such as polyaniline, polythiophene and polypyrrole, and laminate of such an inorganic or organic electrically-conductive material with ITO. Preferred among these materials is electrically-conductive metal oxide. In particular, ITO is preferred from the standpoint of productivity, electrical conductivity, transparency, etc. The thickness of the anode may be properly predetermined depending on the kind of the anode material. In practice, however, it is preferably from 10 nm to 5 $\mu$m, more preferably from 50 nm to 1 $\mu$m, even more preferably from 100 nm to 500 nm.

The anode is normally formed as a layer on a soda lime glass, alkali-free glass, transparent resin substrate or the like. The glass, if used, is preferably alkali-free glass to minimize the amount of ions eluted therefrom. The soda lime glass, if used, is preferably provided with a barrier coat of silica or the like. The thickness of the substrate is not specifically limited so far as it is great enough to maintain the desired mechanical strength. If the substrate is glass, its thickness is normally not less than 0.2 mm, preferably not less than 0.7 mm.

The preparation of the anode can be accomplished by a proper method depending on the anode material used. For example, if the anode material is ITO, electron beam method, sputtering method, resistance heating metallizing method, chemical reaction method (e.g., sol-gel method), method involving the application of a dispersion of indium tin oxide, or the like may be employed. The anode thus prepared can be cleaned or otherwise treated to lower the driving voltage of the device or raise the light-emitting efficiency of the device. For example, if the anode material is ITO, UV-ozone treatment, plasma treatment or the like is effective.

The cathode supplies electron into the electron-injecting layer, electron-transporting layer, light-emitting layer, etc. The form of the cathode is predetermined according to the adhesivity of the cathode to the adjacent layer such as electron-injecting layer, electron-transporting layer and light-emitting layer, the ionization potential of the cathode, the stability of the cathode, etc. The cathode may be formed by a metal, alloy, metal halide, metal oxide, electrically-conductive compound or mixture thereof. Specific examples of such a material include alkaline metal (e.g., Li, Na, K), fluoride thereof, alkaline earth metal (e.g., Mg, Ca), fluoride thereof, gold, silver, lead, aluminum, sodium-potassium alloy, mixture thereof, lithium-aluminum alloy, mixture thereof, magnesium-silver alloy, mixture thereof, and rare earth metal such as indium and ytterbium. Preferred among these materials are those having a work function of not more than 4eV. More desirable among these materials are aluminum, lithium-aluminum alloy, mixture thereof, magnesium-silver alloy, and mixture thereof. The cathode may have either a single-layer structure made of the foregoing compounds or mixture thereof or a laminated structure containing the foregoing compounds or mixture thereof. The thickness of the cathode may be properly predetermined depending on the kind of the cathode material. In practice, however, it is preferably from 10 nm to 5 $\mu$m, more preferably from 50 nm to 1 $\mu$m, even more preferably from 100 nm to 1 $\mu$m.

The preparation of the cathode can be accomplished by electron beam method, sputtering method, resistance heating metallizing method, coating method or the like. A single metal may be evaporated. Alternatively, two or more metals may be evaporated at the same time. Further, a plurality of metals mat be evaporated at the same time to form an alloy electrode. Alternatively, an alloy which has been previously prepared may be evaporated. The sheet resistivity of the anode and cathode is preferably as low as not greater than several hundreds of $\Omega/\square$.

The light-emitting layer may be made of any material capable of forming a layer which acts to receive positive holes from the anode or positive hole-injecting layer or positive hole-transporting layer while receiving electron from the cathode or electron-injecting layer or electron-transporting layer under the application of electric field, allows the electric charge thus injected to move and provide a site for the recombination of positive hole and electron to emit light. Examples of such a material include compounds of the present invention, benzoxazole derivative, benzoimidazole derivative, benzothiazole derivative, styrylbenzene derivative, polyphenyl derivative, diphenylbutadiene derivative, tetraphenylbutadiene derivative, naphthalimide derivative, coumarin derivative, perylene derivative, perinone derivative, oxadiazole derivative, aldazine derivative, pyralidine derivative, cyclopentadiene derivative, bisstyrylanthracene derivative, quinacridone derivative, pyrrolopyridine derivative, thiadiazolopyridine derivative, cyclopentadiene derivative, styrylamine derivative, organic silicon derivative, organic boron derivative, aromatic dimethylidine compound, various metallic complexes such as metallic complex of 8-quinolinol derivative and rare earth complex, and polymer compound such as polythiophene, polyphenylene and polyphenylvinylene. The thickness of the light-emitting layer is not specifically limited. In practice, however, it is preferably from 1 nm to 5 $\mu$m, more preferably from 5 nm to 1 $\mu$m, even more preferably from 10 nm to 500 nm.

The method for the formation of the light-emitting layer is not specifically limited. In practice, however, resistance heating metallizing method, electron beam method, sputtering method, molecular lamination method, coating method (spin coating method, casting method, dip coating method, etc.), LB method, ink jet process or the like maybe used. Preferred among these methods are resistance heating metallizing method and coating method.

The positive hole-injecting layer and positive hole-transporting layer may be formed by any material capable of injecting positive holes from the anode, transporting positive holes or providing barrier against electron injected from the cathode. Specific examples of such a material include electrically-conductive high molecular weight oligomers such as carbazole derivative, triazole derivative, oxazole derivative, oxadiazole derivative, imidazole derivative, polyarylalkane derivative, pyrazoline derivative, pyrazolone derivative, phenylenediamine derivative, arylamine derivative, amino-substituted chalcone derivative, styrylanthracene derivative, fluorenone derivative, hydrazone derivative, stilbene derivative, silazane derivative, aromatic tertiary amine compound, styrylamine compound, aromatic dimethylidene compound, porphiline compound, polysilane compound, poly(N-vinylcarbazole) derivative, aniline copolymer, thiophene oligomer and polythiophene. The thickness of the positive hole-injecting layer and positive hole-transporting layer is not specifically limited. In practice, however, it is preferably from 1 nm to 5 $\mu$m, more preferably from 5 nm to 1 $\mu$m, particularly preferably from 10 nm to 500 nm. The positive hole-injecting layer and positive hole-transporting layer may have either a single-layer structure comprising one or more of the foregoing materials or a multi-layer structure comprising a plurality of layers having the same or different compositions.

The formation of the positive hole-injecting layer and positive hole-transporting layer can be accomplished by vacuum evaporation method, ink jet method, LB method, or method involving the application of a solution or dispersion of the foregoing positive hole-injecting and transporting materials in a solvent (spin coating method, casting method, dip coating method, etc.). If coating method is used, these positive hole-injecting and transporting materials may be dissolved or dispersed with a resin component. Examples of such a resin component include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, and silicone resin.

The electron-injecting layer and electron-transporting layer may be formed by any material capable of injecting electron from the cathode, transporting electron or providing barrier against positive holes injected from the anode. Specific examples of such a material include metallic complexes of compounds of the present invention, triazole derivative, oxazole derivative, oxadiazole derivative, fluorenone derivative, anthraquinone dimethane derivative, anthrone derivative, diphenylquinone derivative, thiopyran dioxide derivative, carbodimide derivative, fluorenilidenemethane derivative, distyrylpyrazine derivative, heterocylic tetracarboxylic anhydride such as naphthaleneperylene and phthalocyanine derivative, and metallic complexes having as ligands metal phthalocyanine, benzoxazole or benzothiazole. The thickness of the electron-injecting layer and electron-transporting layer is not specifically limited. In practice, however, it is preferably from 1 nm to 5 $\mu$m, more preferably from 5 nm to 1 $\mu$m, even more preferably from 10 nm to 500 nm. The electron-injecting layer and electron-transporting layer may have either a single-layer structure comprising one or more of the foregoing materials or a multi-layer structure comprising a plurality of layers having the same or different compositions.

The formation of the electron-injecting layer and electron-transporting layer can be accomplished by vacuum evaporation method, ink jet method, LB method, method involving the application of a dispersion of the foregoing electron-injecting and transporting material (spin coating method, casting method, dip coating method, etc.), or the like may be employed. If coating method is used, these materials may be dissolved or dispersed with a resin component. As such a resin component there may be used those exemplified with reference. to the positive hole-injecting and transporting layers.

The protective layer may be formed by any material capable of preventing the device from being contaminated by materials which accelerate the deterioration of the device such as water content and oxygen. Specific examples of such a material include-metal such as In, Sn, Pb, Au, Cu, Ag, Ti and Ni, metal oxide such as MgO, SiO, $SiO_2$, $Al_2O_3$, GeO, NiO, CaO, BaO, $Fe_2O_3$, $Y_2O_3$ and $TiO_2$, metal fluoride such as $MgF_2$, LiF, $AlF_3$ and $CaF_2$, polyethylene, polypropylene, polymethylene methacrylate, polyimide, polyurea, polytetrafluoroethylene, polychlorotrifluoroethylene, polydichlorodifluoroethylene, copolymer of chlorotrifluoroethylene with dichlorodifluoroethylene, copolymer obtained by the copolymerization of a monomer mixture containing tetrafluoroethylene and at least one comonomer, fluorine-containing copolymer having a cyclic structure in its main chain, hygroscopic material having a percent water absorption of not less than 1%, and moisture proof material having a percent water absorption of not more than 0.1%.

The method for the formation of the protective layer is not specifically limited. For example, vacuum evaporation method, sputtering method, reactive sputtering method, MBE (molecular beam epitaxy) method, cluster ion beam method, ion plating method, plasma polymerization method (high frequency-excited ion plating method), plasma CVD method, laser CVD method, thermal CVD method, gas source CVD method, coating method, etc. may be used.

The present invention will be further described in the following examples, but the present invention should not be construed as being limited thereto.

Synthesis of Compound (1-1)

To 12.2 g of salicylic acid were added 100 ml of ethyl acetate and 0.5 ml of dimethylformamide. The mixture was then a stirred at room temperature. To the mixture was then added dropwise 8.46 ml of oxalyl dichloride. The mixture was then stirred for 30 minutes. To the solution thus obtained were then added 15 g of benzoin and 24.4 ml of triethylamine. The mixture was then stirred for 3 hours. To the reaction solution were then added 200 ml of ethyl acetate and 300 ml of water. The resulting organic phase was then separated. The organic phase thus separated was washed twice with 300 ml of a 1N hydrochloric acid, with 300 ml of water and then with 100 ml of saturated brine, and then dried over sodium sulfate. The organic phase was concentrated to obtain a crude product which was then purified through column chromatography (hexane/ethyl acetate) to obtain 5 g of a compound a.

To 5 g of the compound a were then added 30 ml of acetic acid and 2.3 g of sodium acetate. The mixture was then stirred under reflux for 4 hours. The mixture was then allowed to cool to room temperature. The solid matter thus precipitated was filtered off, and then washed with water and methanol. The solid matter was then recrystallized from a mixture of chloroform and methanol to obtain 2.2 g of a compound b.

To 1 g of the compound b was then added 5 ml of ethanol. To the mixture was then added 0.28 g of zinc acetate dihydrate. The mixture was then stirred under reflux for 3 hours. The mixture was then allowed to cool to room temperature. The solid matter thus precipitated was filtered off, and then washed with ethanol to obtain 0.4 g of a white solid matter (1-1) which fluoresces blue. The white solid matter was then measured for fluorescent spectrum in dichloroethane. As a result, the white solid matter exhibited λmax of 432 nm.

Synthesis of Compound (1-2)

To 1 g of the compound b was added 5 ml of ethanol. To the solution was then added 0.20 g of triisopropoxy aluminum. The mixture was then stirred under reflux for 3 hours. The mixture was then allowed to cool to room temperature. The solid matter thus precipitated was filtered off, and then washed with ethanol to obtain 0.4 g of a white sold matter (1-2) which fluoresces blue. The solid matter was then measured for fluorescent spectrum in dichloroethane. As a result, the solid matter exhibited λmax of 478 nm.

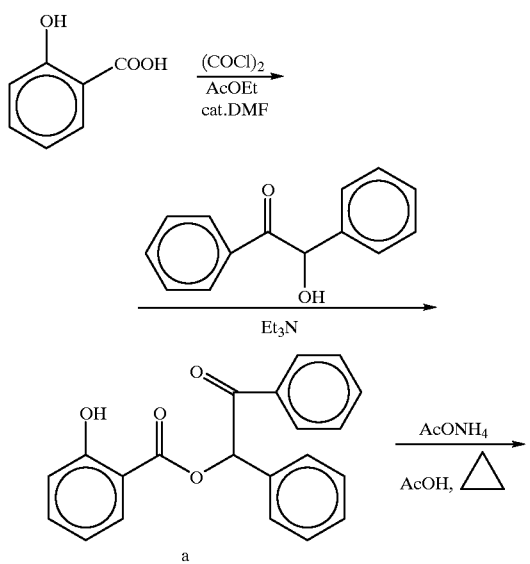

a

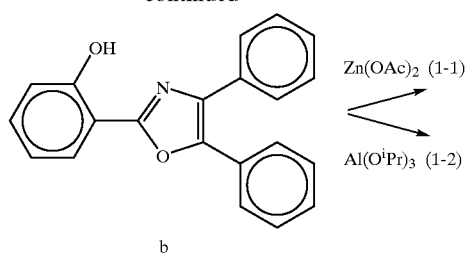

b

Synthesis of Compound (1-3)

To 5.8 g of salicylaldehyde were added 50 ml of acetic acid and 11 g of ammonium acetate. The mixture was then stirred under reflux for 4 hours. The mixture was then allowed to cool to room temperature. The solid matter thus precipitated was filtered off, and then washed with methanol. The solid matter was then recrystallized from a mixture of chloroform and methanol to obtain 4.1 g of a compound c.

To 2 g of the compound c thus obtained was then added 10 ml of ethanol. To the solution was then added 0.7 g of zinc acetate dihydrate. The mixture was then stirred under reflux for 3 hours. The mixture was then allowed to cool to room temperature. The solid matter thus precipitated was filtered off, and then washed with ethanol to obtain 0.6 g of a white solid matter (1-3) which fluoresces blue. The solid matter thus obtained was then measured for fluorescent spectrum in dichloroethane. As a result, the solid matter exhibited λmax of 405 nm.

Synthesis of Compound (1-4)

To 2 g of the compound b was added 10 ml of ethanol. To the solution was then added 0.43 g of triisopropoxy aluminum. The mixture was then stirred under reflux for 3 hours. The mixture was then allowed to cool to room temperature. The solid matter thus precipitated was filtered off, and then washed with ethanol to obtain 0.5 g of a white solid matter (1-4) which fluoresces blue. The solid matter thus obtained was then measured for fluorescent spectrum in dichloroethane. As a result, the solid matter exhibited λmax of 449 nm.

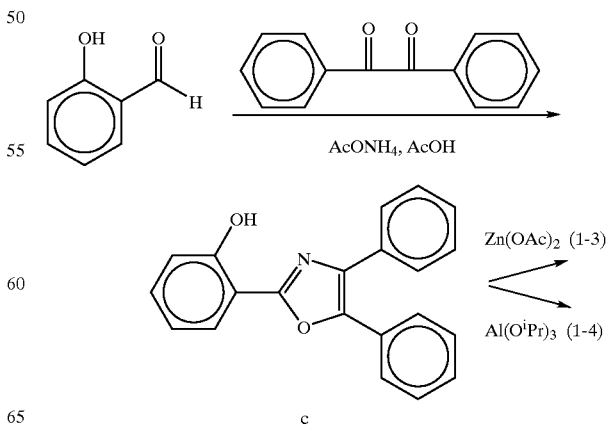

c

Synthesis of Compound (2-1)

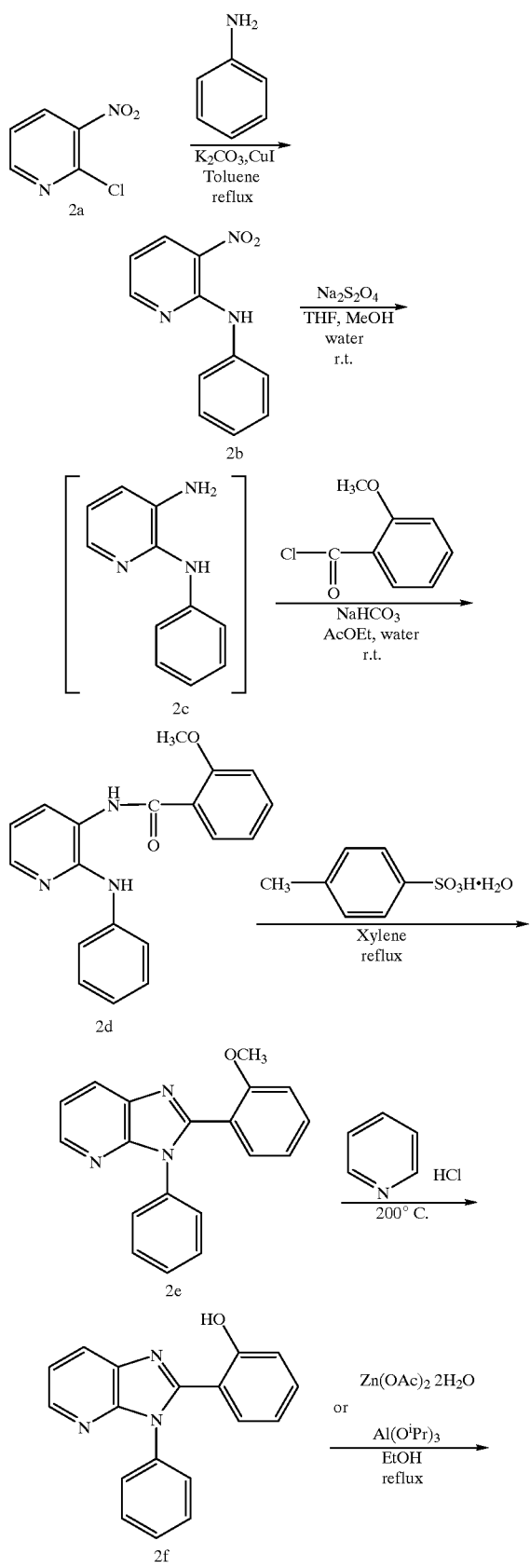

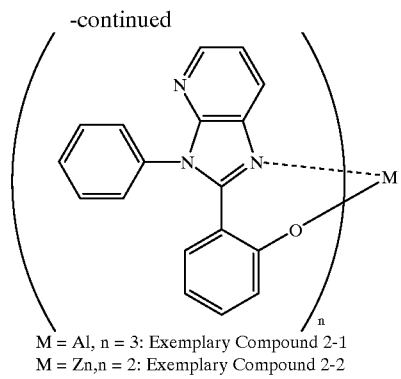

M = Al, n = 3: Exemplary Compound 2-1
M = Zn, n = 2: Exemplary Compound 2-2

1) Synthesis of Compound 2b 45.7 g (0.490 mol) of aniline was added to a mixture of 50.8 g (0.320 mol) of 2-chloro-3-nitropyridine, 90.8 g (0.657 mol) of potassium carbonate, 7.90 g (0.0416 mol) of copper iodide (I) and 300 ml of toluene with stirring at room temperature in an atmosphere of nitrogen. The mixture was then heated under refluxed for 5 hours. The reaction solution was then filtered. The resulting filtrate was then concentrated under reduced pressure. The residue was purified through silica gel column chromatography (developing solvent: chloroform), and then recrystallized from a mixture of chloroform and hexane to obtain 45.7 g (0.21 mol) of a compound 2b. (Yield: 66%)

2) Synthesis of Compound 2d 16.0 g (0.0743 mol) of the compound 2b was dissolved in a mixture of 160 ml of tetrahydrofuran and 40 ml of methanol. To the solution was then added dropwise a solution of 65.1 g (0.374 mol) of sodium hydrosulfite in 220 ml of water with stirring at room temperature in an atmosphere of nitrogen. After 1 hour of stirring, 180 ml of ethyl acetate was then added to the solution. Subsequently, to the solution was added dropwise a solution of 13.6 g (0.162 mol) of sodium hydrogencarbonate in 130 ml of water. To the solution was then added dropwise a solution of 12.0 g (0.070 mol) of 2-methoxybenzoyl chloride in 50 ml of ethyl acetate. The mixture was then stirred at room temperature for 5 hours. To the solution was then added saturated brine. The resulting organic phase was then separated. The aqueous phase was extracted with ethyl acetate. The resulting organic phase was washed with saturated brine. The organic phase was then separated. The organic phase was dried over anhydrous magnesium sulfate, concentrated, and then recrystallized from a mixture of ethyl acetate and n-hexane to obtain 18.3 g (0.0573 mol) of the desired compound 2d. (Yield: 82%)

3) Synthesis of Compound 2e 200 ml of xylene was added to a mixture of 18.3 g (0.0573 mol) of the compound 2d and 2.3 g (0.0121 mol) of p-toluenesulonic monohydride. The mixture was then heated under reflux in an atmosphere of nitrogen for 6 hours so that it was subjected to azeotropic dehydration. The reaction solution was concentrated under reduced pressure, purified through silica gal column chromatography (developing solvent: chloroform), and then recrystallized from a mixture of chloroform and acetonitrile to obtain 5.6 g (0.0186 mol) of the desired compound 2e. (Yield: 32%)

4) Synthesis of Compound 2f 4.30 g (0.0143 mol) of the compound 2e and 10.0 g (0.0865 mol) of pyridine hydrochloride were heated to an external temperature of 200° C. with stirring in an atmosphere of nitrogen for 4 hours. The reaction solution was purified through silica gel column chromatography (developing solvent: chloroform), and then recrystallized from a mixture of chloroform, acetonitrile and n-hexane to obtain 3.50 g (0.0122 mol) of the desired compound 2e. (Yield: 85%)

5) Synthesis of Exemplary Compound 2-1

1.19 g (4.14 mmol) of the compound 2f was dissolved in 20 ml of ethanol. To the solution were then added 281 mg (1.38 mmol) of triisopropoxy aluminum and 5 ml of ethanol. The mixture was then heated under reflux for 3 hours. The reaction solution was then allowed to cool to room temperature. The solid matter thus precipitated was filtered off, and then washed with ethanol to obtain 0.85 g (0.959 mmol) of Exemplary Compound 2-1. (Yield: 69%; melting point: 228–230° C.)

Synthesis of Compound (2-2)

1.44 g (5.91 mmol) of the compound 2f was dissolved in 20 ml of ethahol. To the solution were then added 549 mg (2.50 mmol) of zinc acetate dihydrate and 5 ml of ethanol. The mixture was then heated under reflux for 4 hours. The reaction solution was then allowed to cool temperature. The solid matter thus precipitated was filtered off, and then washed with ethanol to obtain 1.36 g (2.13 mmol) of Exemplary Compound 2-2. (Yield: 85%; melting point: 249–251° C. (decomposition)) Preparation and evaluation of EL device:

COMPARATIVE EXAMPLE 1

A cleaned ITO substrate was placed in a vacuum evaporator where TPD (N,N'-diphenyl-N,N'-di(m-tolyl)-benzidine) was then evaporated thereonto to a thickness of 40 nm. Thereafter, Compound A (Zn(OXZ)$_2$) and Alq (tris (8-hydroxyquinoline) aluminum complex were evaporated onto the substrate to a thickness of 50 nm and 10 nm, respectively. With a patterned mask (light-emitting area: 5 mm×5 mm) placed on the organic thin film layer, magnesium and silver were then co-evaporated at a ratio of 10:1 to a thickness of 50 nm in the vacuum evaporator. Silver was then evaporated onto the substrate to a thickness of 50 nm to prepare a light-emitting device.

Using a Type 2400 source measure unit produced by Toyo Technica Co., Ltd., a constant dc voltage was applied to the EL device to cause light emission. The luminance was measured by means of a Type BM-8 produced by TOPCON CORP. The wavelength of-light thus emitted was measured by means of a Type PMA-11 spectral analyzer produced by Hamamatsu Photonics K.K.

As a result, the EL device was found to emit light having a color-purity as low as ELmax of 475 nm and a chromaticity (x, y) of 0.20 and 0.24, respectively, at a maximum luminance of 895 cd/m$^2$ (9 V).

COMPARATIVE EXAMPLE 2

A cleaned ITO substrate was placed in a vacuum evaporator where TPD (N,N'-diphenyl-N,N'-di(m-tolyl)-benzidine) was then evaporated thereonto to a thickness of 40 nm. Thereafter, Compound B (DPVBi) was evaporated onto the substrate to a thickness of 60 nm. With a patterned mask (light-emitting area: 5 mm×5 mm) placed on the organic thin film layer, magnesium and silver were then co-evaporated at a ratio of 10:1 to a thickness of 50 nm in the vacuum evaporator. Silver was then evaporated onto the substrate to a thickness of 50 nm.

A voltage was then applied to the light-emitting device thus prepared. However, the light-emitting device emitted only a weak blue light.

COMPARATIVE EXAMPLE 3

A cleaned ITO substrate was placed in a vacuum evaporator where TPD (N,N'-diphenyl-N,N'-di(m-tolyl)-benzidine) was then evaporated thereonto to a thickness of 40 nm. Thereafter, Compound C was evaporated onto the substrate to a thickness of 20 nm. Compound A was then evaporated onto the substrate to a thickness of 40 nm. With a patterned mask (light-emitting area: 5 mm×5 mm) placed on the organic thin film layer, magnesium and silver were then co-evaporated at a ratio of 10:1 to a thickness of 50 nm in the vacuum evaporator. Silver was then evaporated onto the substrate to a thickness of 50 nm. A voltage was then applied to the light-emitting device thus prepared. As a result, the light-emitting device emitted light having ELmax of 455 nm and a chromaticity (x, y) of (0.15) and (0.20)980 cd/m$^2$, respectively.

COMPARATIVE EXAMPLE 4

A cleaned ITO substrate was placed in a vacuum evaporator where TPD (N,N'-diphenyl-N,N'-di(m-tolyl)-benzidine) was then evaporated thereonto to a thickness of 40 nm. Thereafter, Alq (Tris(quinolinato)aluminum and Compound D were co-evaporated onto the substrate at a ratio of 100:1 to a thickness of 20 nm. Alq was then evaporated onto the substrate to a thickness of 40 nm. With a patterned mask (light-emitting area: 5 mm×5 mm) placed on the organic thin film layer, magnesium and silver were then co-evaporated at a ratio of 10:1 to a thickness of 50 nmin the vacuum evaporator. Silver was then evaporated onto the substrate to a thickness of 50 nm. A voltage of 8 V was then applied to the light-emitting device thus prepared. As a result, the light-emitting device emitted light having ELmax of 597 nm and a chromaticity (x, y) of (0.54) and (0.44)2620 cd/m$^2$, respectively. The external quantum yield in the vicinity of 100 cd/m$^2$ was calculated. The results were 0.8%.

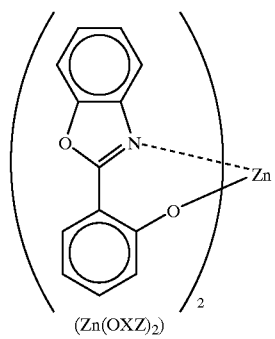

Compound A (Zn(OXZ)$_2$)

-continued

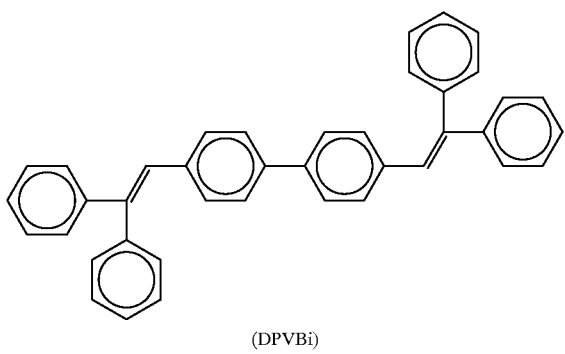

Compound B (DPVBi)

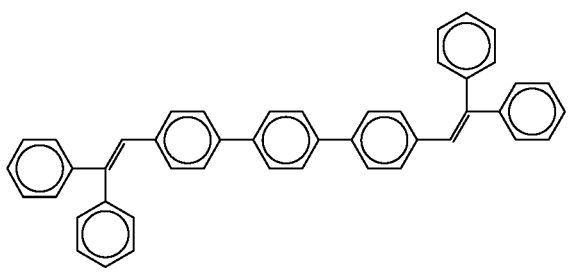

Compound C

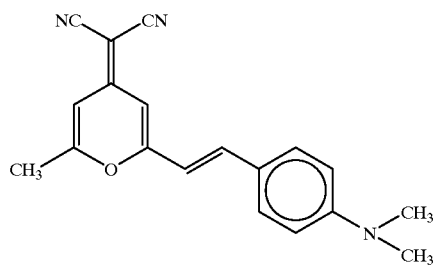

Compound D

EXAMPLE 1

A light-emitting device was prepared in the same manner as in Comparative Example 1 except that Compound (1-1) of the present invention was used instead of Compound A. The light-emitting device thus prepared was then evaluated in the same manner as in Comparative Example 1. When a voltage of 6 V was applied to the light-emitting device, the light-emitting device emitted a blue light having ELmax of 440 nm and a chromaticity (x, y) of 0.15 and 0.11, respectively, at a maximum luminance of 1,010 cd/m$^2$ (11 V). It was thus made obvious that an EL device comprising a light-emitting layer containing an azole compound of the present invention emits a blue light having a high color purity.

EXAMPLE 2

A light-emitting device was prepared in the same manner as in Comparative Example 2 except that Compound (1-1) of the present invention was used instead of Compound B. The light-emitting device thus prepared was then evaluated in the same manner as in Comparative Example 2. When a voltage of 7 V was applied to the light-emitting device, the light-emitting device emitted a blue light having ELmax of 440 nm and a chromaticity (x, y) of 0.15 and 0.10, respectively, at a maximum luminance of 220 cd/m$^2$ (11 V). It was thus made obvious that the azole compound of the present invention can act as a good electron-injecting/transporting material.

EXAMPLE 3

A light-emitting device was prepared in the same manner as in Comparative Example 2 except that Compound (1-4) of the present invention was used instead of Compound B. The light-emitting device thus prepared was then evaluated in the same manner as in Comparative Example 2. When a voltage of 12 V was applied to the light-emitting device, the light-emitting device emitted a blue light having ELmax of 450 nm and a chromaticity (x, y) of 0.15 and 0.15, respectively, at a maximum luminance of 108 cd/m$^2$ (14 V).

EXAMPLE 4

A light-emitting device was prepared in the same manner as in Comparative Example 3 except that Compound (1-1) of the present invention was used instead of Alq. The light-emitting device thus prepared was then evaluated in the same manner as in Comparative Example 3. When a voltage of 12 V was applied to the light-emitting device, the light-emitting device emitted light having ELmax of 450 nm and a chromaticity (x, y) of (0.15) and (0.16)900 cd/m$^2$, respectively.

EXAMPLE 5

A light-emitting device was prepared in the same manner as in Comparative Example 3 except that Compound (2-1) of the present invention was used instead of Alq. The light-emitting device thus prepared was then evaluated in the same manner as in Comparative Example 3. When a voltage of 11 V was applied to the light-emitting device, the light-emitting device emitted light having ELmax of 450 nm and a chromaticity (x, y) of (0.15) and (0.13)1900 cd/m$^2$, respectively.

EXAMPLE 6

A light-emitting device was prepared in the same manner as in Comparative Example 3 except that Compound (2-2) of the present invention was used instead of Alq. The light-emitting device thus prepared was then evaluated in the same manner as in Comparative Example 3. When a voltage of 11 V was applied to the light-emitting device, the light-emitting device emitted light having ELmax of 450 nm and a chromaticity (x, y) of (0.15) and (0.13)1770 cd/m$^2$, respectively.

EXAMPLE 7

A cleaned ITO substrate was placed in a vacuum evaporator where TPD (N,N'-diphenyl-N,N'-di(m-tolyl)-benzidine) was then evaporated thereonto to a thickness of 40 nm. Thereafter, Alq (Tris(quinolinato)aluminum and Compound D were co-evaporated onto the substrate at a ratio of 100:1 to a thickness of 20 nm. Compound (2-1) of the present invention was then evaporated onto the substrate to a thickness of 40 nm. With a patterned mask (light-emitting area: 5 mm×5 mm) placed on the organic thin film layer, magnesium and silver were then co-evaporated at a ratio of 10:1 to a thickness of 50 nm in the vacuum evaporator. Silver was then evaporated onto the substrate to a thickness of 50 nm. A voltage of 8 V was then applied to the light-emitting device thus prepared. As a result, the light-emitting device emitted light having ELmax of 595 nm and a chromaticity (x, y) of (0.54) and (0.44)2710 cd/m², respectively. The external quantum yield in the vicinity of 100 cd/m² was calculated. The results were 1.2%.

EXAMPLE 8

40 mg of a polyvinyl carbazole was dissolved in 3 ml of dichloroethane. The solution was then spin-coated onto a cleaned ITO substrate (2,000 rpm, 10 sec). The organic layer thus formed had a thickness of about 40 nm. The substrate was placed in a vacuum evaporator where Compound C was then evaporated thereonto to a thickness of 20 nm. Compound (2-1) of the present invention was then evaporated onto the substrate to a thickness of 40 nm. With a patterned mask (light-emitting area: 5 mm×5 mm) placed on the organic thin film layer, magnesium and silver were then co-evaporated at a ratio of 10:1 to a thickness of 50 nm in the vacuum evaporator. Silver was then evaporated onto the substrate to a thickness of 50 nm. A voltage of 14 V was then applied to the light-emitting device thus prepared. As a result, the light-emitting device emitted light having ELmax of 450 nm and a chromaticity (x, y) of (0.15) and (0.13)740 cd/m², respectively.

Similarly, EL devices comprising other compounds of the present invention were evaluated. As a result, these EL devices were confirmed to act as blue light-emitting and electron-injecting/transporting materials.

As mentioned above, the compound of the present invention can be used as a blue light-emitting material for organic light-emitting device or electron-injecting/transporting material to provide excellent characteristics such as high efficiency and high color purity. Further, the compound of the present invention fluoresces a highly pure blue color and thus can be used for various fluorescent material or organic light-emitting device for medical purpose.

While the invention has been described in detail and with reference to specific embodiments thereof, it will be apparent to one skilled in the art that various changes and modifications can be made therein without departing from the spirit and scope thereof.

What is claimed is:

1. A compound represented by the following general formula (X):

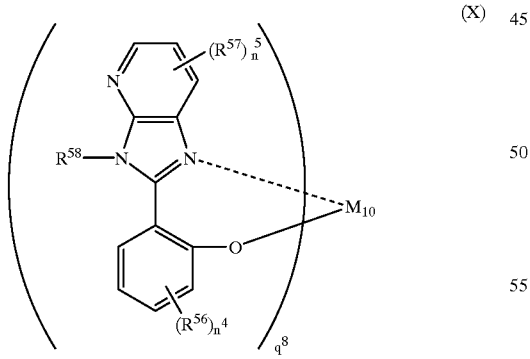

wherein $R^{56}$, $R^{57}$ and $R^{58}$ each represents a substituent, $M^{10}$ represents a metal ion, $q^8$ represents an integer of not less than 2, $n^4$ represents an integer of from 0 to 4, and $n^5$ represents an integer of from 0 to 3.

2. A compound as recited in claim 1, wherein $R^{56}$ and $R^{57}$ each represents an alkyl group, an alkenyl group, an alkinyl group, an aryl group, a substituted carbonyl group, an amino group, a sulfonyl group, a sulfo group, a carboxyl group, a heterocyclic group, a hydroxyl group, an alkoxyl group, an aryloxy group, a halogen atom, a thiol group, an alkylthio group, an arylthio group, a cyano group or a silyl group.

3. A compound as recited in claim 1, wherein $R^{56}$ and $R^{57}$ each represents an alkyl group, an alkenyl group, an aryl group, a heteroaryl group, an alkoxy group or a cyano group.

4. A compound as recited in claim 1, wherein $R^{56}$ and $R^{57}$ each represents an alkyl group or an aryl group.

5. A compound as recited in claim 1, wherein $R^{56}$ and $R^{57}$ each represents an alkyl group.

6. A compound as recited in claim 1, wherein $R^{58}$ represents an alkyl group, an alkenyl group, an alkinyl group, an aryl group, a substituted carbonyl group, a substituted sulfonyl group or a heterocyclic group.

7. A compound as recited in claim 1, wherein $R^{58}$ represents an alkyl group, an aryl group or a heteroaryl group.

8. A compound as recited in claim 1, wherein $R^{58}$ represents an aryl group.

9. A compound as recited in claim 1, wherein $M^{10}$ represents a divalent or trivalent metal ion.

10. A compound as recited in claim 1, wherein $M^{10}$ represents $Be^{2+}$, $Mg^{2+}$, $Al^{3+}$ or $Zn^{2+}$.

11. An organic light-emitting device comprising a pair of electrodes having a light-emitting layer or a plurality of organic thin film layers containing said light-emitting layer formed interposed therebetween, wherein at least one of said plurality of organic thin film layers comprises a compound represented by the following general formula (X) incorporated therein:

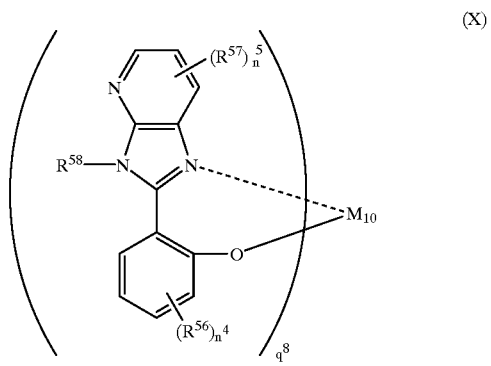

wherein $R^{56}$, $R^{57}$ and $R^{58}$ each represents a substituent, $M^{10}$ represents a metal ion, $q^8$ represents an integer of not less than 2, $n^4$ represents an integer of from 0 to 4, and $n^5$ represents an integer of from 0 to 3.

12. An organic light emitting device as recited in claim 11, wherein $R^{56}$ and $R^{57}$ each represents ail alkyl group, an alkenyl group, an alkinyl group, an aryl group, a substituted carbonyl group, an amino group, a sulfonyl group, a sulfo group, a carboxyl group, a heterocyclic group, a hydroxyl group, an alkoxyl group, an aryloxy group, a halogen atom, a thiol group, an alkylthio group, an arylthio group, a cyano group or a silyl group.

13. An organic light emitting device as recited in claim 11, wherein $R^{56}$ and $R^{57}$ each represents an alkyl group, an alkenyl group, an aryl group, a heteroaryl group, an alkoxy group or a cyano group.

14. An organic light emitting device as recited in claim 11, wherein $R^{56}$ and $R^{57}$ each represents an alkyl group or an aryl group.

15. An organic light emitting device as recited in claim 11, wherein $R^{56}$ and $R^{57}$ each represents an alkyl group.

16. An organic light emitting device as recited in claim 11, wherein $R^{58}$ represents an alkyl group, an alkenyl group, an alkinyl group, an aryl group, a substituted carbonyl group, a substituted sulfonyl group or a heterocyclic group.

17. An organic light emitting device as recited in claim 11, wherein $R^{58}$ represents an alkyl group, an aryl group or a heteroaryl group.

18. An organic light emitting device as recited in claim 11, wherein $R^{58}$ represents an aryl group.

19. An organic light emitting device as recited in claim 11, wherein $M^{10}$ represents a divalent or trivalent metal ion.

20. An organic light emitting device as recited in claim 11, wherein $M^{10}$ represents $Be^{2+}$, $Mg^{2+}$, $Al^{3+}$ or $Zn^{2+}$.

* * * * *